United States Patent [19] — Camenzind et al.

[11] Patent Number: 4,737,302
[45] Date of Patent: Apr. 12, 1988

[54] AMINOMETHYL DERIVATIVES OF BENZOTHIAZOLINETHIONE AS LUBRICANT ADDITIVES

[75] Inventors: Hugo Camenzind, Fribourg, Switzerland; Emyr Phillips, Sale, England

[73] Assignee: Ciba-Geigy Corporation, Ardsley, N.Y.

[21] Appl. No.: 866,189
[22] Filed: May 22, 1986

[30] Foreign Application Priority Data

May 23, 1985 [CH] Switzerland .................. 2199/85

[51] Int. Cl.$^4$ .......................................... C10M 133/38
[52] U.S. Cl. ...................................... 252/47; 252/47.5
[58] Field of Search ............................... 252/47, 47.5

[56] References Cited

FOREIGN PATENT DOCUMENTS 1028924  5/1966  United Kingdom .

OTHER PUBLICATIONS

CRC Handbook of Lubrication, CRC Press, 1984, pp. 301–315.
H. S. Gandhi et al, Applied Catalysis 3, 79 (1982).
A. F. Halasa et al, J. Org. Chem. 36, 636 (1971).

Primary Examiner—William R. Dixon, Jr.
Assistant Examiner—Cynthia A. Prezlock
Attorney, Agent, or Firm—Luther A. R. Hall

[57] ABSTRACT

The invention relates to lubricant compositions comprising
(a) one or more mineral oils or synthetic oils and
(b) 0.05 to 5% by weight of at least one compound of formulae I, II and III

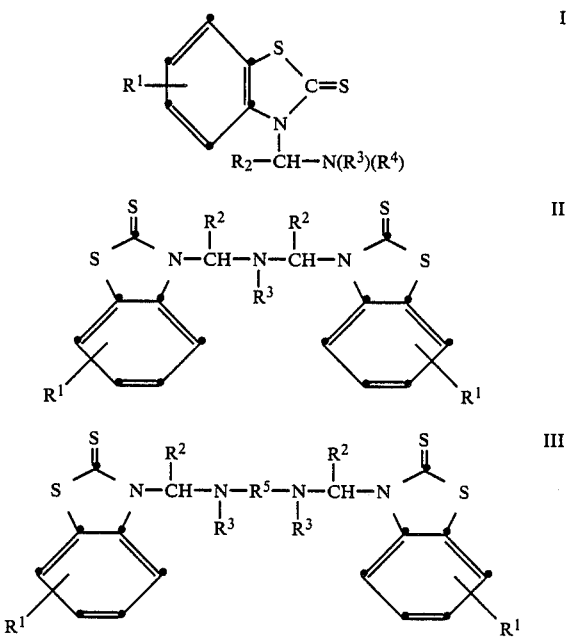

wherein $R^1$, $R^2$, $R^3$, $R^4$ and $R^5$ are as defined in claim 1; and
(c) further optional lubricant additives.

Some of these compounds are new and can be prepared by Mannich reaction from the appropriate 2-mercaptobenzothiazoles, an aldehyde $R^2$—CHO and a primary or secondary mono- or diamine. These Mannich bases are useful additives for lubricants for reducing friction, wear, corrosion and oxidation.

7 Claims, No Drawings

AMINOMETHYL DERIVATIVES OF BENZOTHIAZOLINETHIONE AS LUBRICANT ADDITIVES

The present invention relates to lubricant compositions containing oil-soluble derivatives of benzothiazoline-2-thione as lubricant additives and to the compounds themselves where novel.

It is customary to treat mineral and synthetic lubricants with additives to improve their performance properties. Particularly useful additives are those that protect the machine which it is desired to lubricate from wear. It is required of these additives that they shall increase the load-carrying capacity of the lubricant, that they shall not have a corrosive action on the metal parts to be protected, and that they shall have good heat resistance.

For this utility it is preferred to use phosphorus and sulfur-containing compounds such as salts of dialkyldithiophosphates (q.v. CRC Handbook of Lubrication, Vol. 2 (1984), 301–315, CRC Press Inc.). In view of the use of catalysts in exhaust gas systems of combustion engines, however, the phosphorus content of lubricating oils shall be kept to a minimum to prevent the catalysts from becoming deactivated [H. S. Gandhi et al., Applied Catalysis 3, (1982), 79–82].

It has now been found that the specific oil-soluble derivatives of benzothiazole that are free from phosphorus exhibit excellent properties in mineral and synthetic lubricants with respect to wear, load-carrying capacity, protection of metal parts from corrosion and ash content. In lubricant formulations containing reduced amounts of zinc dialkyldithiophosphates, these derivatives afford substantially better protection against oxidation. Specifically, these compounds are N-aminomethyl derivatives of benzothiazoline-2-thione.

Accordingly, the present invention relates to lubricant compositions which comprise
(a) one or more mineral oils or synthetic oils and
(b) 0.05 to 5% by weight of at least one compound of formula I, II or III

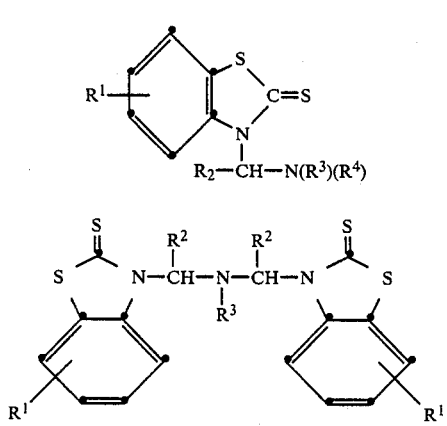

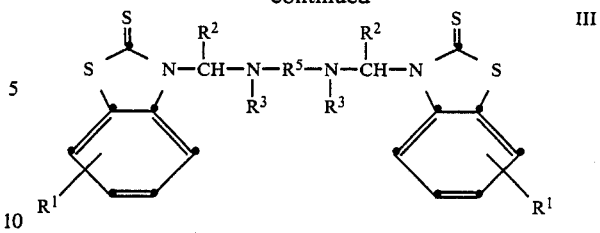

wherein
$R^1$ is hydrogen, $C_1$–$C_{12}$alkyl, $C_2$–$C_4$alkoxy, $C_2$–$C_{24}$alkoxycarbonyl or nitro, $R^2$ is hydrogen, $C_1$–$C_{12}$alkyl, 2-furyl, phenyl or phenyl which is substituted by $C_1$–$C_4$alkyl, $C_1$–$C_4$alkoxy, $C_2$–$C_{24}$alkoxycarbonyl or nitro, $R^3$ and $R^4$ are each independently of the other hydrogen, $C_1$–$C_{20}$alkyl which may be interrupted by one or more members selected from O, S and N or which may contain oxo or thiono groups; or are $C_3$–$C_{24}$alkenyl, $C_3$–$C_{12}$alkoxyalkyl, $C_5$–$C_8$cycloalkyl, phenyl or phenyl which is substituted by $C_1$–$C_{12}$alkyl, $C_1$–$C_4$alkoxy, $C_2$–$C_{24}$alkoxycarbonyl or nitro; or are naphthyl, $C_7$–$C_9$phenylalkyl, 2-furylmethyl or 2-(tetrahydrofuryl)methyl; or $R^3$ and $R^4$, together with the nitrogen atom to which they are attached, form a 5- or 6-membered ring which, in addition to containing the N-atom, may also contain further hetero atoms selected from O, N and S or oxo or thiono groups, or may be fused to a benzene nucleus; and $R^5$ is $C_2$–$C_{12}$alkylene which may be interrupted by O, N or S or may contain oxo or thiono groups; or is $C_6$–$C_{15}$cycloalkylene, $C_6$–$C_{15}$arylene, carbonyl or thiocarbonyl or, in formula III, is the $-N(R^3)-R^5-N(R^3)-$ group a piperazin-1,4-diyl radical which may be substituted by one or more methyl groups, as additives, which reduce friction, wear, corrosion and oxidation in (a); and
(c) further optional lubricant additives.

$R^1$, $R^2$, $R^3$ and $R^4$ as alkyl may be unbranched or branched and are e.g. methyl, ethyl, isopropyl, n-butyl, sec-butyl, tert-butyl, isoamyl, n-hexyl, 2-ethylbutyl, 1-methylpentyl, 1,3-dimethylbutyl, 2-ethylhexyl, isoheptyl, n-octyl, 1-methylheptyl, 1,1,3-trimethylhexyl, n-decyl, 1-methylundecyl or n-dodecyl. $R^3$ and $R^4$ as alkyl may also be tetradecyl, hexadecyl, octadecyl or eicosyl.

$R^1$ and $R^2$ as alkoxy may be methoxy, ethoxy, isopropoxy or n-butoxy.

$R^1$ as alkoxycarbonyl contains 2 to 24 carbon atoms in the alkyl moiety and may be methoxycarbonyl, ethoxycarbonyl or 2-ethylhexoxycarbonyl.

$R^2$, $R^3$ and $R^4$ may be alkoxycarbonyl-substituted phenyl, where alkoxycarbonyl is as defined for $R^1$.

$R^2$, $R^3$ and $R^4$ may be substituted phenyl such as tolyl, xylyl, 4-tert-butylphenyl, 3-methoxyphenyl, 4-propoxyphenyl, 3-butoxycarbonylphenyl, 3-nitrophenyl or 4-methyl-3-nitrophenyl.

$R^3$ and $R^4$ as alkoxyalkyl may be 2-methoxyethyl, 2-isopropoxyethyl, 2-butoxyethyl or 2-octyloxyethyl. $R^3$ and $R^4$ as cycloalkyl may be cyclopentyl, cyclohexyl, 4-methylcyclohexyl or cyclooctyl. $R^3$ and $R^4$ as phenylalkyl may be benzyl, 2-phenylethyl, 1-phenylethyl or 2-phenylpropyl. If $R^3$ and $R^4$, together with the N-atom to which they are attached, form a 5- or 6-membered ring, said ring may be a pyrrolidone, piperidine, morpholine, thiomorpholine, piperazine, indole, tetrahydroquinoline or tetrahydroisoquinoline ring. $R^3$ and $R^4$ as alkenyl may be allyl, methallyl, 1-pentenyl, dodecenyl or octadecenyl.

$R^5$ as alkylene may be unbranched or branched alkylene or may also be interrupted by O, S or N, and is e.g. di-, tri-, tetra-, hexa-, octa-, deca- or dodecamethylene; 2,2,4- or 2,4,4-trimethylhexamethylene, 3-oxapentamethylene, 4-thiaheptamethylene or 4-(methylaza)-heptamethylene.

$R^5$ as cycloalkylene may be 1,4-cyclohexylene, 1,4-decahydronaphthylene, cyclohexane-1,4-dimethylene or dicyclohexylmethane-4,4-diyl. $R^5$ as arylene may be 1,3-phenylene, 1,4-phenylene, 1,4-naphthylene, 4,4'-diphenylene, diphenylmethane-4,4'-diyl or diphenyl oxide-4,4'-diyl.

The sum of the carbon atoms contained in the radicals $R^1$, $R^2$, $R^3$, $R^4$ and $R^5$ is preferably more than 10, most preferably more than 14. These radicals contribute to the solubility in oil.

Lubricant compositions are preferred which comprise 0.1 to 3% by weight of at least one compound of formula I, II or III.

Lubricant compositions are preferred which contain compounds of formula I, II or III, wherein $R^2$ is hydrogen and, in particular, wherein $R^1$ also is hydrogen.

Lubricant compositions are preferred which contain compounds of formula I, II or III, wherein $R^1$ and $R^2$ are hydrogen, $R^3$ and $R^4$ are each independently of the other hydrogen, $C_1$–$C_{24}$alkyl, $C_3$–$C_{24}$alkenyl, cyclohexyl, phenyl, phenyl which is substituted by $C_1$–$C_{12}$alkyl or $C_1$–$C_{24}$alkoxycarbonyl, or are $C_7$–$C_{10}$phenylalkyl, 2-methoxyethyl or 3-methoxypropyl, and $R^5$ is $C_2$–$C_{12}$alkylene.

Lubricant compositions are most preferred which contain a compound of formula

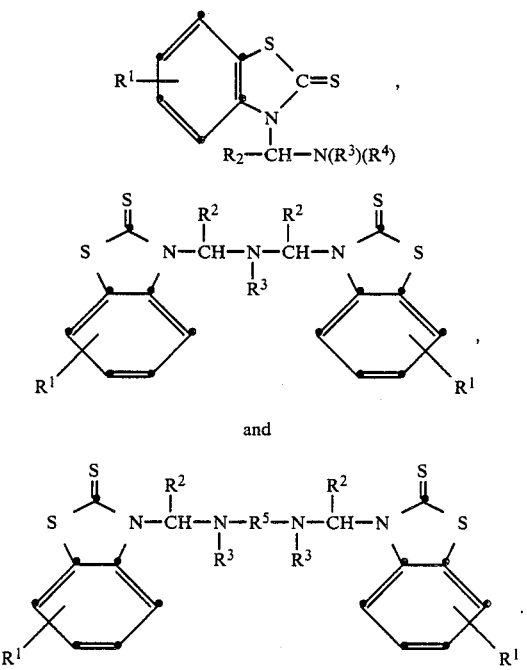

Examples of eligible compounds of formula I are:
3-[bis(2-ethylhexyl)aminomethyl]benzothiazoline-2-thione 3-(dicyclohexylaminomethyl)benzothiazoline-2-thione
3-(diphenylaminomethyl)benzothiazoline-2-thione
3-[bis(4-dodecylphenyl)aminomethyl]benzothiazoline-2-thione
3-[dibenzylaminomethyl]benzothiazoline-2-thione
3-[N-(1-naphthylo)phenylaminomethyl]benzothiazoline-2-thione
3-[N-(2-furylmethyl)butylaminomethyl]benzothiazoline-2-thione
3-[N-(2-tetrahydrofurylmethyl)hexylaminomethyl]benzothiazoline-2-thione
3-[bis(2-methoxyethyl)aminomethyl]benzothiazole-2-thione
3-(piperidinomethyl)benzothiazoline-2-thione
3-(pyrrolidinomethyl)benzothiazoline-2-thione
3-(morpholinomethyl)benzothiazoline-2-thione
3-[(2,3-dihydroindolyl)methyl]benzothiazoline-2-thione
3-[(1,2,3,4-tetrahydroquinolyl)methyl]benzothiazoline-2-thione
3-(phenylaminomethyl)benzothiazoline-2-thione
3-[(4-dodecylphenyl)aminomethyl]benzothiazoline-2-thione
3-[bis(2-ethylhexyl)aminomethyl]5-carbethoxybenzothiazoline-2-thione.

Examples of compounds of formula II are:
N,N-bis(2-thionobenzothiazolin-3-ylmethyl)-2-ethylhexylamine
N,N-bis(2-thionobenzothiazolin-3-ylmethyl)-n-dodecylamine
N,N-bis(2-thionobenzothiazolin-3-ylmethyl)-3-ethoxypropylamine.

Examples of compounds of formula III are:
N,N'-bis(2-thionobenzothiazolin-3-ylmethyl)-N,N'-dimethylethylenediamine
N,N'-bis(2-thionobenzothiazolin-3-ylmethyl)piperazine
N,N'-bis(2-thionobenzothiazolin-3-ylmethyl)-2,5-dimethylpiperazine
N,N'-bis(2-thionobenzothiazolin-3-ylmethyl)-4,4'-diaminodicyclohexylmethane
N,N'-bis(2-thionobenzothiazolin-3-ylmehyl)-p-phenylenediamine.

The lubricants for which the additives of this invention are suitable may be lubricating oils or greases based on mineral oils or on synthetic oils or mixtures thereof. Examples of synthetic oils are ester oils, olefin polymers or ethylene oxide polymers.

The additives can also be dissolved beforehand in a small quantity of oil and the concentrate so obtained is then added to the lubricant.

In addition to containing the additives of formula I, II or III, the lubricant may also contain other additives customarily employed for lubricants. Examples of such additives are antioxidants, metal passivators, corrosion inhibitors, viscosity improvers, pour-point depressants, dispersants, surfactants, or other antiwear additives. For lubricating greases, thickeners are added to the oils.

Examples of antioxidants are:
(a) Alkylated and non-alkylated aromatic amines and mixtures thereof, for example: dioctyldiphenylamine, mono-tert-octylphenyl-α- and -β-naphthylamines, phenotriazine, dioctylphenothiazine, phenyl-α-naphthylamine, N,N'-di-sec-butyl-p-phenylenediamine.
(b) Sterically hindered phenols, for example: 2,6-di-tert-butyl-p-cresol, 4,4'-bis(2,6-diisopropylphenol), 2,4,6-triisopropylphenol, 2,2'-thiobis(4-methyl-6-tert-butylphenol), 4,4'methylene-bis(2,6-di-tert-butylphenol).

(c) Esters of thiodipropionic acid or thiodiacetic acid, for example: dilaurylthiodipropionate or dioctylthiodiacetate.

(d) Salts of carbamic and dithiophosphoric acids, for example: antimony diamyldithiocarbamate, zinc diamyldithiophosphate.

Examples of metal deactivators are:
(a) for copper, e.g.: benzotriazole, tetrahydrobenzotriazole, 2-mercaptobenzotriazole, 2,5-dimercaptothiadiazole, salicyclidene propylenediamine, salts of salicylaminoguanidine.
(b) for lead, e.g.: sabacic acid derivatives, quinizarine, propyl gallate.

Examples of rust inhibitors are:
(a) Organic acids, the esters, metal salts and anhydrides thereof, e.g.: N-oleyl sarcosine, sorbitan monooleate, lead naphthenate, dodecenylsuccinic anhydride.
(b) Nitrogen-containing compounds for example: Primary, secondary or tertiary aliphatic or cycloaliphatic amines and amine salts or organic and inorganic acids, for example oil-suluble alkylammonium carboxylates. Heterocyclic compounds, e.g. substituted imidazolines and oxazolines.
(c) Sulfur-containing compounds, for example: barium dinonylnaphthalenesulfonates, calcium petroleum sulfonates.

Examples of viscosity index improvers are:
polymethacrylates, vinyl pyrrolidone/methacrylate copolymers,
polybutene, olefin copolymers, styrene/acrylate copolymers.

Examples of pour-point depressants are:
alkylated naphthalenes, alkylated phenols, polymethacrylates.

Examples of surfactants and dispersants are:
polyalkenylsuccinimides, oil-soluble metal soaps such as calcium, barium, magnesium and aluminium carboxylates, phenolates or sulfonates.

Examples of other antiwear additives are:
Compounds containing sulfur and/or phosphorus and/or halogen, e.g. sulfurised vegetable oils, zinc dialkyl dithiophosphates, tritolylphosphate, chlorinated paraffins, alkyl and aryl disulfides.

Some of the compounds of formula I, II or III are known and some are novel compounds. Known compounds of formula I are those wherein $R^1$ and $R^2$ are hydrogen and $R^3$ and $R^4$ together contain not more than 14 carbon atoms. Such compounds are obtained by a Mannich reaction of 2-mercaptobenzothiazole with formaldehyde and a primary or secondary amine.

Halasa and Smith, J. Org. Chem. 36 (1971), 636–641, have shown that, under the customary conditions of Mannich reactions, the aminomethylation of 2-mercaptobenzothiazole takes place at the N-atom of the tautomeric form of benzothiazoline-2-thione.

Among the compounds of formulae I, II and III, those compounds are novel in which $R^1$ or $R^2$ is not hydrogen. Among the compounds of formula I, those compounds are novel wherein (a) $R^1$ and $R^2$ are hydrogen and $R^3$ and $R^4$ together contain more than 14 carbon atoms, as well as those in which (b) $R^1$ and $R^2$ are hydrogen, $R^3$ and $R^4$ are aliphatic or cycloaliphatic radicals and together contain more than 10 carbon atoms. Among the compounds of formula II, those compounds are novel in which the radicals $R^2$ and $R^3$ together contain more than 10 carbon atoms. Among the compounds of formula III, those compounds are novel in which $R^5$ is not an arylene radical.

The invention therefore also relates to compounds of formula I

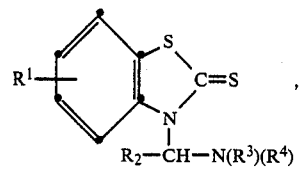

wherein $R^1$ is $C_1$–$C_{12}$alkyl, $C_1$–$C_4$alkoxy, $C_2$–$C_{24}$alkoxycarbonyl or nitro and $R^2$, $R^3$ and $R^4$ are as previously defined.

Preferred compounds of formula I are those wherein $R^2$ is hydrogen.

Particularly preferred compounds of formula I are those wherein $R^1$ and $R^2$ are hydrogen, $R^3$ and $R^4$ are as previously defined and together contain more than 14 carbon atoms.

The most preferred compounds of formula I are those wherein $R^1$ and $R^2$ are hydrogen, $R^3$ and $R^4$ are each independently of the other hydrogen, $C_1$–$C_{24}$alkyl, $C_3$–$C_{24}$alkenyl, $C_3$–$C_{12}$alkoxyalkyl or $C_5$–$C_8$cycloalkyl, and $R^3$ and $R^4$ together contain more than 10 carbon atoms and, preferably, wherein $R^3$ and $R^4$ each independently of the other are $C_6$–$C_{12}$alkyl or cyclohexyl or both are 2-ethylhexyl.

The invention further relates to compounds of formula II

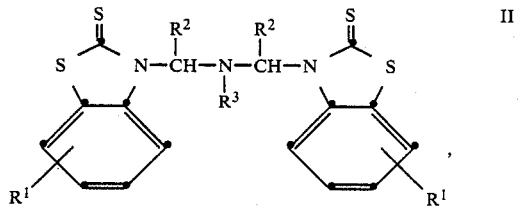

wherein $R^1$ is $C_1$–$C_{12}$alkyl, $C_1$–$C_4$alkoxy, $C_2$–$C_{24}$alkoxycarbonyl or nitro, and $R^2$ and $R^3$ are as previously defined.

Preferred compounds of formula II are those wherein $R^2$ is hydrogen. Particularly preferred compounds of formula II are those wherein $R^1$ and $R^2$ are hydrogen and $R^3$ contains more than 10 carbon atoms.

The invention also relates to compounds of formula III

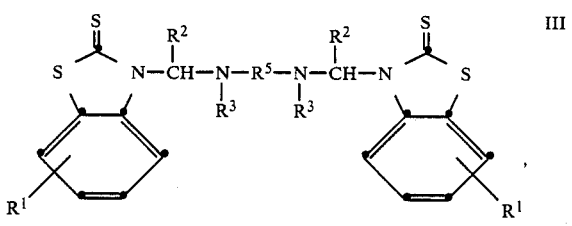

wherein $R^1$ is $C_1$–$C_{12}$alkyl, $C_1$–$C_4$alkoxy, $C_2$–$C_{24}$alkoxycarbonyl or nitro, and $R^2$, $R^3$ and $R^5$ are as previously defined.

Preferred compounds of formula III are those wherein $R^2$ is hydrogen. Particularly preferred compounds of formula III are those wherein $R^1$ and $R^2$ are hydrogen and $R^3$ and $R^5$ are as previously defined, with the proviso that $R^5$ is not arylene; and, most particularly, compounds of formula III in which $R^3$ is hydrogen, $C_1$-$C_{24}$alkyl or $C_3$-$C_{24}$alkenyl, and $R^5$ is $C_2$-$C_{12}$alkylene.

The compounds of formula I are obtained by reaction of a 2-mercaptobenzothiazole of formula IV with a monoamine $R^3$—NH—$R^4$ and an aldehyde $R^2$—CHO:

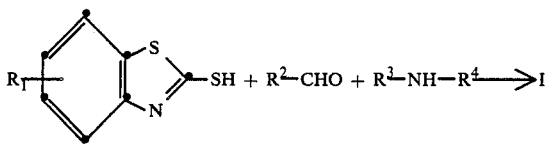

The amine can be a primary or secondary monoamine and the reaction is carried out in approximately equimolar ratio with a small excess of aldehyde. The preferred reaction medium is a non-polar solvent, preferably toluene, cyclohexane or ligroin. However, it is also possible to use a polar solvent, in particular an alcohol such as ethanol or methanol. As described by Halasa and Smith, it is also possible first to form the appropriate water-soluble amine salt of formula IV and then to react this salt, in aqueous medium, with the aldehyde.

The compounds of formula II are prepared by reaction of IV with $R^2$—OH and a primary monoamine $R^3$—$NH_2$ in the molar ratio 2:2:1:

$$2IV + 2R^2\text{—CHO} + R^3\text{—}NH_2 \rightarrow \qquad II$$

The compounds of formula III are prepared by Mannich reaction using a diamine $R^3$—NH—$R^5$—NH—$R^3$:

$$2IV + 2R^2\text{—CHO} + R^3\text{—NH—}R^5\text{—NH—}R^3 \rightarrow \qquad III$$

The diamine may be a primary or secondary diamine. It is preferred to use a primary diamine ($R^3$=H).

The following Examples serve to illustrate the invention.

EXAMPLE 1

Mannich reaction in methanol/water

To a suspension of 250.8 g (1.5 moles) of 2-mercaptobenzothiazole in 1500 ml of methanol are added 112.8 ml (1.5 moles) of 37% aqueous formaldehyde, followed by the dropwise addition, with stirring, of 362.4 g (1.5 moles) of bis(2-ethylhexyl)amine. The mixture is stirred for 15 hours at 50° C. and then concentrated by evaporation in vacuo, affording as residue 618 g of 3-[bis(2-ethylhexyl)aminomethyl]benzothiazoline-2-thione as a reddish brown oil Analysis calculated: C 68.52%, H 9.58%, N 6.66%, S 15.24%, found: 68.36%, 9.57%, 6.69%, 15.29%.

EXAMPLE 2

Mannich reaction in ethanol/water

With stirring, 18.63 (0.2 mole) of aniline are added to a suspension of 33.45 g (0.2 mole) of 2-mercaptobenzothiazole in 120 ml of ethanol, the temperature rising to 30° C. Then 16.4 g (0.2 mole) of 37% aqueous formaldehyde solution are added and stirring is continued for 30 minutes. The precipitate is isolated by filtration and washed with cold ethanol and hexane, affording 47 g of 3-(phenylaminomethyl)benzothiazoline-2-thione which melts at 102°-103° C.

Analysis calculated: C 61.74%, H 4.44%, N 10.29%, S 23.54%, found: 61.53%, 4.43%, 10.10%, 23.79%.

In similar manner, 3-(dodecylphenylaminomethyl)-benzothiazoline-2-thione is obtained as a brown oil starting from technical dodecylaniline (mixture of isomers).

EXAMPLE 3

Mannich reaction in toluene/water 10.12 g (13.7 ml; 0.01 mole) of dipropylamine and 8.3 g (7.6 ml; 0.1 mole) of 36% aqueous formaldehyde are added dropwise to a suspension of 16.7 g (0.1 mole) of 2-mercaptobenzothiazole in 40 ml of toluene. The mixture is stirred vigorously for 5 hours at 50° C. The small aqueous phase is separated and the toluene phase is concentrated by evaporation in vacuo, affording as residue 26.4 g of yellowish orange crystals of 3-(dipropylaminomethyl)benzothiazoline-2-thione which melts at 60°-62° C.

Analysis calculated: C 59.96%, H 7.19%, N 9.99%, S 22.86%, found: 59.82%, 7.20%, 9.89%, 22.86%.

The Examples listed in the subsequent Tables 1-3 are carried out in corresponding manner. In these Tables
method A=procedure according to Example 1
method B=procedure according to Example 2
method C=procedure according to Example 3.

In the column "Analysis", the data in the first line always indicate the theoretical values and the data in the second line the values found (in percentages).

TABLE 1

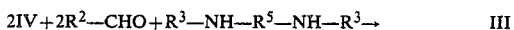

| Example | $-N\begin{array}{c}R^1\\ \diagdown\\ R^2\end{array}$ | Preparatory method | Yield (g) | Aspect | m.p. (°C.) | Analysis (%) C | H | N | S |
|---|---|---|---|---|---|---|---|---|---|
| 1 | $-N-\!\!\left[\begin{array}{c}CH_2-CH-(CH_2)_3-CH_3\\ \mid\\ CH_2CH_3\end{array}\right]_2$ | A/C | 98/97 | dark yellow viscous oil | — | 68.52 68.36 | 9.58 9.57 | 6.66 6.69 | 15.24 15.29 |

TABLE 1-continued

[Structure: benzothiazole-2-thione with N-CH2-N(R1)(R2) substituent]

| Example | -N(R1)(R2) | Preparatory method | Yield (g) | Aspect | m.p. (°C.) | C | H | N | S |
|---|---|---|---|---|---|---|---|---|---|
| 2 | —NH—C6H5 | B | 89 | beige-coloured crystalline solid | 102–103 | 61.74 / 61.53 | 4.44 / 4.43 | 10.29 / 10.10 | 23.54 / 23.79 |
| 3 | —N(CH2CH2CH3)2 | C | 94 | yellowish orange crystalline solid | 60–62 | 59.96 / 59.82 | 7.19 / 7.20 | 9.99 / 9.89 | 22.86 / 22.86 |
| 4 | mixture: —NHC14H27, —NHC12H25 | C | 95 | brown oil | — | 66.62 / 66.51 | 9.05 / 9.25 | 7.40 / 7.62 | 16.93 / 16.96 |
| 5 | —NH—(C6H4-C12H25) mixture of isomers | B | 92 | dark brown viscous oil | — | 70.86 / 71.22 | 8.23 / 8.33 | 6.36 / 6.14 | 14.55 / 14.19 |
| 6 | —N(CH2CH2CH2CH3)2 | C | 92 | brown oil | — | 62.29 / 62.32 | 7.84 / 7.83 | 9.08 / 8.91 | 20.78 / 20.87 |
| 7 | —N(CH2CH(CH3)2)2 | C | 91 | beige-coloured crystalline solid | 102–106 | 62.29 / 62.89 | 7.84 / 7.66 | 9.08 / 9.07 | 20.78 / 21.05 |
| 8 | —N(C13H27)2 | C | 97 | brownish yellow oil | — | 72.8 / 72.60 | 10.78 / 10.73 | 4.99 / 4.88 | 11.43 / 11.41 |
| 9 | —N(C18H37)2 | C | 99 | yellow crystalline solid | 65 | 75.36 / 75.56 | 11.50 / 11.54 | 3.99 / 3.98 | 9.14 / 9.16 |
| 10 | —N(CH3)(CH2—C6H5) | B | 95 | brown viscous oil | — | 63.97 / 63.93 | 5.37 / 5.42 | 9.32 / 9.13 | 21.34 / 21.10 |
| 11 | —N(CH2CH3)(CH2—C6H5) | B | 92 | yellow crystalline solid | 85–87 | 64.93 / 64.52 | 5.77 / 5.75 | 8.76 / 8.76 | 29.39 / 21.08 |
| 12 | —N(CH2—C6H5)2 | B | 90 | yellow crystalline solid | 96–98 | 70.18 / 70.05 | 5.35 / 5.43 | 7.44 / 7.37 | 17.03 / 17.22 |
| 13 | —N (piperidino) | B | 97 | yellow crystalline solid | 152–156 | 59.05 / 59.04 | 6.10 / 6.10 | 10.60 / 10.27 | 24.25 / 24.26 |
| 14 | —N O (morpholino) | B | 79 | yellow crystalline solid | 134–137 | 54.11 / 54.12 | 5.30 / 5.25 | 10.52 / 10.01 | 24.07 / 24.77 |

TABLE 1-continued

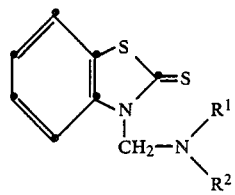

| Example | -N(R¹)(R²) | Preparatory method | Yield (g) | Aspect | m.p. (°C.) | C | H | N | S |
|---|---|---|---|---|---|---|---|---|---|
| 15 | $-N{+}CH_2CH_2-O-CH_3)_2$ | B | 96 | brownish yellow oil | — | 53.82 / 53.93 | 6.45 / 6.51 | 8.97 / 8.75 | 20.52 / 19.91 |

TABLE 2

| Example | Compound | Preparatory method | Yield (g) | Aspect | C | H | N | S |
|---|---|---|---|---|---|---|---|---|
| 16 | (ethyl ester benzothiazole-2-thione with di-(2-ethylhexyl)aminomethyl) | C | 95 | brown oil | 65.81 / 65.95 | 9.00 / 9.22 | 5.68 / 5.59 | 13.01 / 12.90 |
| 17 | (6-nitro benzothiazole-2-thione with di-(2-ethylhexyl)aminomethyl) | C | 95 | orange-red oil | 61.90 / 62.12 | 8.44 / 8.56 | 9.02 / 8.97 | 13.77 / 13.55 |

TABLE 3

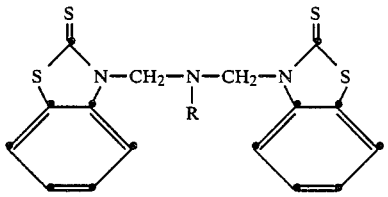

| Example | -N-R | Preparatory method | Yield (g) | Aspect | m.p. (°C.) | C | H | N | S |
|---|---|---|---|---|---|---|---|---|---|
| 18 | $-N-CH_2-CH(CH_2CH_3)-(CH_2)_3-CH_3$ | C | 97 | brown viscous oil | — | 59.1 / 59.09 | 5.99 / 6.08 | 8.62 / 8.27 | 26.29 / 25.81 |
| 19 | $N-C_{18}H_{37}$ | C | 88 | yellow crystalline solid | 90–92 | 65.02 / 65.19 | 7.86 / 7.94 | 6.69 / 6.52 | 20.42 / 20.31 |
| 20 | $N-C_{18}H_{35}$ | C | 99 | pale yellow wax | — | — / — | — / — | — / 6.68 | — / 20.35 |

TABLE 3-continued

| Example | —N—R | Preparatory method | Yield (g) | Aspect | m.p. (°C.) | Analysis (%) C | H | N | S |
|---|---|---|---|---|---|---|---|---|---|
| 21 | N—CH₂—(phenyl) | C | 93 | yellow crystalline solid | 158–163 | 59.32 / 61.14 | 4.11 / 4.54 | 9.02 / 8.34 | 27.54 / 25.80 |

EXAMPLE 22

Antiwear test

The antiwear test is carried out by ASTM Standard Method D 2783-81 using the Shell four-ball machine. The base oil employed in the test is Catenex ® P 941 (ex Shell). The values obtained are (a) the weld load (WL), i.e. the load (in kg) at which welding of the 4 balls occurs over 10 seconds, and (b) the wear scar diameter (WSD) at a load of 40 kg over 1 hour (in mm).

1% by weight of additive is used in all test samples. The results are reported in Table 4.

TABLE 4

| Additive from Example | WL (kg) | WSD (mm) |
|---|---|---|
| 1 | 180 | 0.55 |
| 3 | 200 | 0.60 |
| 5 | 180 | 0.55 |
| 6 | 180 | 0.55 |
| 7 | 180 | 0.60 |
| 8 | 200 | 0.55 |
| 9 | 180 | 0.60 |
| 10 | 180 | 0.60 |
| 12 | 180 | 0.60 |
| 15 | 180 | 0.65 |
| 16 | 180 | 0.55 |
| 17 | 200 | 0.50 |
| 19 | 180 | 0.60 |
| 20 | 200 | 0.60 |
| — | 160 | 0.90 |

EXAMPLE 23

Test for copper deactivation

A brightly polished copper plate measuring 60×10×1 mm is immersed in turbine oil which contains 50 ppm of dissolved sulfur as well as 0.5% of 3-[bis(2-ethylhexyl)aminomethyl]benzothiazoline-2-thione. A comparison sample contains no thiazoline derivative. The samples are heated to 100° C. for 2 hours. The copper plates are then washed with petroleum ether, dried, and the colour is determined in accordance with ASTM D 130 by comparison with a standard colour chart. Evaluation is made by a rating of 1-4:

1—untarnished
2—moderate tarnish
3—pronounced tarnish
4—corrosion

Result:

colour of sample 1B
comparison sample 3B

EXAMPLE 24

Oxidation stabilising test (TFOUT Test: Thin-film Oxygen Uptake Test)

This test is a modified version of the Rotary Bomb Oxidation Test for Mineral Oils (ASTM D 2272). A full description will be found in C. S. Ku and S. M. Hau, A thin-Film Oxygen Uptake Test for the Evaluation of Automotive Crankcase Lubricants, *Lubrication Engineering*, Vol. 40 (2), 75–83 (1984). The test oil is a mineral oil-based motor oil that contains half the usual amount of zinc dithiophos-phate (0.75%: zinc content 0.06%, based on the motor oil). This change was made in order to be able to show a potential effect of the stabiliser to be tested.

Two commercially available 15 W40 motor oils with an adjusted content of zinc dithiophosphate (ZDTP) are used as base oil:

oil A: 0.063% of phosphorus in the form of primary and secondary ZDTP (in the ratio 1:1)
oil B: 0.067% of phosphorus in the form of primary and secondary ZDTP (in the ratio ratio 2:1).

The additive prepared in Example 1 is tested in the described motor oil in the presence of 2% of water, of a liquid, oxidised, nitrated fraction of a motor fuel as catalyst (4% concentration), of a liquid naphthenate as further catalyst (4% concentration; water and the two liquid catalysts were supplied under the No. Standard Reference Material 1817 by the National Bureau of Standards (NBS) with certificate of analysis). The test is complete when a distinct dip appears in the pressure/time diagram. The results reported in the following table indicate the time (in minutes) to the dip in the pressure/time diagram.

Lengthy times mean good stabiliser effectiveness. Concentration of the stabiliser: 0.5% by weight, based on the oil.

| Formulation | Induction period [time (in minutes) to the distinct drop in pressure] |
|---|---|
| oil A | 95 |
| oil A + 0.5% additive | 170 |
| oil B | 105 |
| oil B + 0.5% additive | 170 |

What is claimed is:

1. A lubricant composition stabilized to reduce friction, wear, corrosion and oxidation, which comprises
   (a) one or more mineral oils or synthetic oils, and
   (b) 0.05 to 5% by weight, based on the oil, of at least one compound of formula I

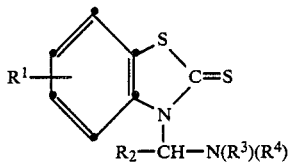

wherein
   $R^1$ is hydrogen, $C_1$-$C_{12}$alkyl, $C_2$-$C_4$alkoxy, $C_2$-$C_{24}$alkoxycarbonyl or nitro,
   $R^2$ is hydrogen, $C_1$-$C_{12}$alkyl, 2-furyl, phenyl or phenyl which is substituted by $C_1$-$C_4$alkyl, $C_1$-$C_4$alkoxy, $C_2$-$C_{24}$alkoxycarbonyl or nitro, and
   $R^3$ and $R^4$ are each independently of the other hydrogen, $C_1$-$C_{20}$alkyl, said alkyl interrupted by one or more members selected from O, S and N atoms or said alkyl containing oxo or thiono groups, or are $C_3$-$C_{24}$alkenyl, $C_3$-$C_{12}$alkoxyalkyl, $C_5$-$C_8$cycloalkyl, phenyl or phenyl which is substituted by $C_1$-$C_{12}$alkyl, $C_1$-$C_4$alkoxy, $C_2$-$C_{24}$alkoxycarbonyl or nitro; or are naphthyl, $C_7$-$C_9$phenylalkyl, 2-furylmethyl or 2-(tetrahydrofuryl)methyl; or $R^3$ and $R^4$, together with nitrogen atom to which they are attached, form a 5- or 6-membered ring containing the N-atom, or said ring additionally containing further hetero atoms selected from O, N and S atoms or containing oxo or thiono groups, or said ring fused to a benzene nucleus.

2. A lubricant composition according to claim 1, comprising 0.1 to 3% by weight of at least one compound of formula I.

3. A lubricant composition according to claim 1, which contains a compound of formula I, wherein the sum of the carbon atoms contained in the radicals $R^1$, $R^2$, $R^3$, and $R^4$ is more than 10.

4. A lubricant composition according to claim 1, which contains a compound of formula I, wherein $R^2$ is hydrogen.

5. A lubricant composition according to claim 4, which contains a compound of formula I, wherein $R^1$ is hydrogen.

6. A lubricant composition according to claim 5, which contains a compound of formula I, wherein $R^3$ and $R^4$ are each independently of the other hydrogen, $C_1$-$C_{24}$alkyl, Chd 3-$C_{24}$alkenyl, cyclohexyl, phenyl, phenyl which is substituted by $C_1$-$C_{12}$alkyl or $C_2$-$C_{24}$alkoxycarbonyl, or are $C_7$-$C_{10}$-phenylalkyl, 2-methoxyethyl or 3-methoxypropyl and $R^5$ is $C_2$-$C_{12}$alkylene.

7. A lubricant composition according to claim 1, which contains a compound of formula I of formula

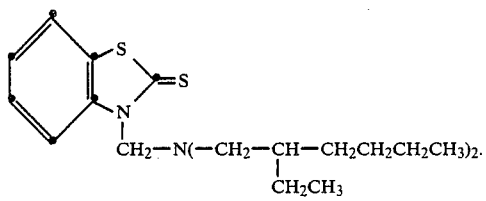

* * * * *